United States Patent [19]

O'Brien et al.

[11] Patent Number: 5,087,726

[45] Date of Patent: Feb. 11, 1992

[54] CARBAMATE ACAT INHIBITORS

[75] Inventors: Patrick M. O'Brien, Northville; Drago R. Sliskovic, Ypsilanti, both of Mich.

[73] Assignee: Warner-Lambert Company, Morris Plains, N.J.

[21] Appl. No.: 479,313

[22] Filed: Feb. 13, 1990

[51] Int. Cl.$^5$ .......................................... C07C 271/42
[52] U.S. Cl. ........................................ 560/25; 560/30;
560/49; 568/412; 568/416; 568/585; 568/631;
549/13; 549/356; 549/429; 548/250; 548/255;
548/262.2; 548/300; 548/335; 548/356;
548/373; 548/400; 546/112; 546/184; 544/179;
544/180; 544/224; 544/242
[58] Field of Search ............... 560/37, 20, 21, 28,
560/30, 31, 49, 64, 65, 158, 163, 161, 174;
568/412, 416, 585, 631, 644, 659, 661, 663;
544/179, 180, 224, 235, 242, 253, 336, 349, 358;
546/112, 184; 548/280, 285, 287, 262.2, 262.4,
300, 308, 335, 347, 356, 369, 373, 400, 452, 469;
549/13, 14, 15, 18, 19, 23, 29, 30, 32, 34-35, 49,
50, 356, 357, 362, 367, 368, 377, 396, 398, 429,
430, 431, 434, 456, 462, 464

[56] References Cited

FOREIGN PATENT DOCUMENTS 1434826 5/1946 United Kingdom .

*Primary Examiner*—José G. Dees
*Assistant Examiner*—D. D. Carr
*Attorney, Agent, or Firm*—Ruth H. Newtson

[57] ABSTRACT

This invention relates to novel compounds which are ACAT inhibitors rendering them useful in lowering blood cholesterol levels. The compounds are carbamates represented by the general formula

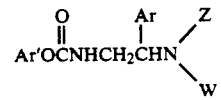

wherein Ar and Ar' represent phenyl or naphthyl each of which may be substituted; m and n each represent zero or one; Z and Y are hydrogen, aliphatic hydrocarbon, heterocyclic, aryl or carbocyclic containing groups.

4 Claims, No Drawings

CARBAMATE ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain carbamate compounds which inhibit the enzyme acyl-coenzyme A:cholesterol acyltransferase (ACAT), pharmaceutical compositions containing these compounds, and a method of treating hypercholesterolemia and atherosclerosis. This invention also describes novel intermediates useful in preparing the pharmaceutically active compounds of this invention.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE

British Patent 1,434,826 described carbamate compounds having the general formula

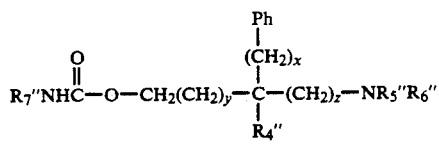

wherein Ph is phenyl substituted with two substituents selected from halogen, methoxy or trifluoromethyl; x, y and z are zero or one; $R_4$ is hydrogen, lower alkyl $C_1-C_6$, cycloalkyl or aryl; $R_5$ and $R_6$ are hydrogen, lower alkyl ($C_1-C_6$), or aralkyl or $NR_5R_6$ together form a ring optionally containing an additional heteroatom; $R_7$ is alkyl $C_1-C_6$, heteroaryl, phenyl or phenyl substituted with one or more substituents selected from alkyl $C_1-C_6$, halogen, alkoxy $C_1-C_6$, nitro or amino. The following specific carbamate compounds are disclosed:
$C_6H_5NHC(=O)OCH_2C(C_6H_5)(C_2H_5)N(CH_3)_2$;
$H_3CNHC(=O)OCH_2C(C_6H_6)(C_2H_5)N(CH_3)_2$;
$H_3CNHC(=O)OCH_2CH(C_6H_5)N(CH_3)_2$;
$C_6H_5NHC(=O)OCH_2CH(C_6H_5)N(CH_3)_2$;
$H_3CNHC(=O)OCH_2CH(C_6H_5)N(CH_3)(CH_2C_6H_5)$;
$CH_6H_5NHC(=O)OCH_2CH(C_6H_5)NHCH_3$;
$C_6H_5NHC(=O)OCH_2CH(C_6H_5)NC_5H_{10}$; and
$C_6H_5NHC(=O)OCH_2CH(C_6H_5)N(CH_3)(CH_2C_6H_5)$.
These compounds inhibit spasms and peristalsis of the gastrointestinal musculature.

SUMMARY OF THE INVENTION

The present invention provides a class of compounds which have acyl-CoA: cholesterol acyltransferase (ACAT) inhibitory activity and intermediates useful in preparing said compounds having the following formula:

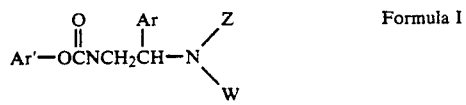

wherein Ar is selected from:

(a) phenyl which is unsubstituted or is substituted with from one to three substituents selected from alkyl having from one to six carbon atoms and which is straight or branched; alkoxy having from one to six carbon atoms and which is straight or branched, alkoxy having from one to six carbon atoms and which is straight or branched;
  phenoxy,
  hydroxy,
  fluorine,
  chlorine,
  bromine,
  nitro,
  trifluoromethyl,
  —COOH,
  —COOalkyl wherein alkyl has from one to four carbon atoms
  —$NR_1R_2$ wherein $R_1$ and $R_2$ are independently hydrogen or alkyl of from one to four carbon atoms;

(b) 1- or 2-naphthyl which is unsubstituted or substituted with: alkyl having from one to six carbon atoms and which is straight or branched; alkoxy having from one to six carbon atoms and which is straight or branched,
  hydroxy,
  fluorine,
  chlorine,
  bromine,
  nitro,
  trifluoromethyl,
  —COOH,
  —COOalkyl wherein alkyl has from one to four carbon atoms —$NR_1R_2$ wherein $R_1$ and $R_2$ are as defined above; and (c) a 5- or 6-membered monocyclic or fused bicyclic heterocycle containing at least one to four nitrogen, oxygen or sulfur atoms in at least one ring member; wherein Ar' is selected from:

(a) phenyl which is unsubstituted or is substituted with from one to three substituents selected from alkyl having from one to six carbon atoms and which is straight or branched; alkoxy having from one to six carbon atoms and which is straight or branched, phenoxy,
hydroxy,
fluorine,
chlorine,
bromine,
nitro,
trifluoromethyl,
—COOH,
—COOalkyl wherein alkyl has from one to four carbon atoms
—$NR_1R_2$ wherein $R_1$ and $R_2$ are independently hydrogen or alkyl of from one to four carbon atoms; and (b) 1- or 2-naphthyl which is unsubstituted or substituted with: alkyl having from one to six carbon atoms and which is straight or branched; alkoxy having from one to six carbon atoms and which is straight or branched, hydroxy,
fluorine,
chlorine,
bromine,
nitro,
trifluoromethyl,
—COOH,
—COOalkyl wherein alkyl has from one to four carbon atoms
—$NR_1R_2$ wherein $R_1$ and $R_2$ are as defined above; wherein Z is selected from:

 (a)

 (b)

R—CH$_2$—; and (c)

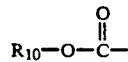 (d)

wherein $R_{10}$ is straight or branched lower alkyl having from one to four carbon atoms; wherein X is oxygen or sulfur; wherein Ar" has the same meaning as Ar'; wherein R is selected from:

(a) a straight or branched hydrocarbon chain having from one to twenty carbon atoms and which is saturated or contains from one to three double bonds;

(b) a straight or branched hydrocarbon chain having from one to six carbon atoms wherein the terminal carbon atom is substituted with chlorine, fluorine, bromine, straight or branched lower alkoxy having from one to four carbon atoms, straight or branched thioalkoxy having from one to four carbon atoms, a $COOR_4$ group wherein $R_4$ is hydrogen or a straight or branched alkyl having from one to four carbon atoms, an —$NR_5R_6$ group wherein $R_5$ and $R_6$ are independently hydrogen or lower alkyl having from one to four carbon atoms, wherein said alkyl is unsubstituted or substituted with hydroxy, or wherein —$NR_5R_6$ taken together form a monocyclic heterocyclic group selected from pyrrolidine, piperidine, piperazine or piperazine substituted in the 4-position with a lower alkyl having from one to four carbon atoms or —$COOR_4$ wherein $R_4$ has the meaning defined above; and (c) a 5- or 6- membered monocyclic or fused bicyclic heterocycle containing at least one to four nitrogen, oxygen or sulfur atoms in at least one ring member;

(d) the group

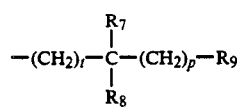

wherein t is zero to four; p is zero to four with the proviso that the sum of t and p is not greater than five; $R_7$ and $R_8$ are independently selected from hydrogen or alkyl having from one to six carbon atoms, or when $R_7$ is hydrogen, $R_8$ can be the same as $R_9$ and $R_9$ is phenyl or phenyl substituted with from one to three substituents selected from straight or branched alkyl having from one to six carbon atoms, straight or branched alkoxy having from one to four carbon atoms, straight or branched thioalkoxy having from one to four carbon atoms, phenoxy, hydroxy, fluorine, chlorine, bromine, nitro, trifluoromethyl, —COOH, COOalkyl wherein alkyl has from one to four carbon atoms, or —$NR_5R_6$ wherein $R_5$ and $R_6$ have the meanings defined above;

(e) phenyl or phenyl substituted with from one to three substitutes selected form straight or branched alkyl having from one to six carbon atoms, straight or branched alkoxy having from one to four carbon atoms, straight or branched thioalkoxy having from one to four carbon atoms, phenoxy, hydroxy, fluorine, chlorine, bromine, nitro, trifluoromethyl, —COOH, COOalkyl whrein alkyl has from one to four carbon atoms, or —$NR_5R_6$ wherein $R_5$ and $R_6$ have the meanings defined above; wherein W is selected from:

(a) hydrogen;

(b) a straight or branched hydrocarbon chain having from one to twenty carbon atoms and which is saturated or contains from one to three double bonds;

(c) a straight or branched hydrocarbon chain having from one to six carbon atoms wherein the terminal carbon atom is substituted with chlorine, fluorine, bromine, straight or branched lower alkoxy having from one to four carbon atoms, straight or branched thioalkoxy having from one to four carbon atoms; a $COOR_4$ group wherein $R_4$ is hydrogen or a straight or branched alkyl having from one to four carbon atoms, an —$NR_5R_6$ group wherein $R_5$ and $R_6$ are independently hydrogen or lower alkyl having from one to four carbon atoms wherein said alkyl is unsubstituted or substituted with hydroxy, or wherein —$NR_5R_6$ taken together form a monocyclic heterocyclic group selected from pyrrolidines, piperidine, piperazine or piperazine substituted in the 4-position with a lower alkyl having from one to four carbon atoms or —$COOR_4$ wherein $R_4$ has the meaning defined above; and (d) the group

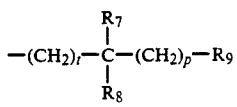

wherein t, p, $R_7$, $R_8$, and $R_9$ have the meanings defined above;

(e) phenyl or phenyl substituted with from one to three substitutes selected form straight or branched alkyl having from one to six carbon atoms, straight or branched alkoxy having from one to four carbon atoms, straight or branched thioalkoxy having from one to four carbon atoms, phenoxy, hydroxy, fluorine, chlorine, bromine, nitro, trifluoromethyl, —COOH, COOalkyl whrein alkyl has from one to four carbon atoms, or —$NR_5R_6$ wherein $R_5$ and $R_6$ have the meanings defined above; or a pharmaceutically acceptable salt or an N-oxide thereof with the proviso that both Z and W are the group

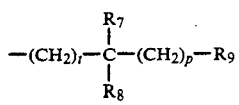

$R_8$ and $R_9$ are not the same.

This invention also provides pharmaceutical compositions containing the compounds of Formula I and methods of treating hypercholesterolemia and atherosclerosis using the compounds of Formula I.

DETAILED DESCRIPTION OF INVENTION

The compounds of the present invention provide a novel class of carbamates which are ACAT Inhibitors, rendering them useful in treating hypercholesterolemia and atherosclerosis.

Illustrative examples of a straight or branched saturated hydrocarbon chain having from one to twenty carbon atoms include methyl, ethyl n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of a straight or branched hydrocarbon chain having from one to twenty carbon atoms and having from one to three double bonds are ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from one to six carbon atoms include, for example, methoxy, ethoxy, n-propoxy, t-butoxy, and pentyloxy.

Illustrative of straight or branched thioalkoxy groups having from one to four carbon atoms are methylthio, ethylthio, n-propylthio, isopropylthio, and butylthio. The thioalkoxy group may also be referred to as alkylthio.

A 5- or 6-membered monocyclic or fused bicyclic heterocycle is a monocyclic or fused bicyclic aromatic ring containing at least one to four hetero atoms in at least one ring, such as nitrogen, oxygen or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, oxazolyl, isoxazolyl, triazolyl, tetrazolyl, imidazolyl, benzothiazolyl, indolyl, quinolinyl, isoquinolinyl, or N-oxides of a heterocycle containing a nitrogen atom.

More specifically, such a heterocycle may be a 2-or 3-thienyl; 2- or 3-furanyl; 2-, 3-, or 4-pyridyl or -pyridyl-N-oxide; 2-, 4-, or 5-pyrimidinyl; 3- or 4-pyradazinyl; 2-pyrazinyl; 2- or 3-pyrrolyl; 3-, 4-, or 5-pyrazolyl, 3-, 4- or 5-isothiazolyl; 5-tetrazolyl; 3- or 5-(1,2,4-triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Preferred compounds of this invention are those wherein Ar' is phenyl or substituted phenyl and more preferably phenyl substituted on the 2,6-positions. Also preferred are compounds wherein Z is

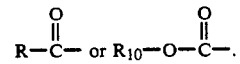

Compounds wherein W is hydrogen are also preferred.

Pharmaceutically acceptable salts of the compounds of Formula I are also included as a part of the present invention.

The acid salts may be generated from the free base by reaction of the latter with one equivalent of a suitable nontoxic, pharmaceutically acceptable acid, followed by evaporation of the solvent employed for the reaction and recrystallization of the salt, if required. The free base may be recovered from the acid salt by reaction of the salt with an aqueous solution of a suitable base such as sodium carbonate, sodium bicarbonate, potassium carbonate, sodium hydroxide, and the like.

Suitable acids for forming acid salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts.

(See, for example, Stephen N. Berge, et al. *J. Pharm. Sciences*, 66:1–19 (1977).

The compounds of the present invention may also exist in different stereoisomeric forms by virtue of the presence of one or more asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

The compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field, F. J. and Salone, R. G., *Biochemica et Biophysica* 712: 557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes. For example, the compounds of Example 1 had an $IC_{50}$ value, i.e. the concentration of test compound required to inhibit 50% expression of the enzyme of 0.51 nm.

The compounds are also evaluated in an in vivo screen, designated APCC, wherein male Sprague-Dawley rats (200 to 225 g) are randomly divided into treatment groups and dosed at 4 PM with either vehicle (CMC/Tween) or suspensions of compounds in vehicle. The normal, chow diet is then replaced with the PCC diet with either 1% or 0.5% cholic acid, as indicated. The rats consume this diet ad libitum during the night and are sacrificed at 8 AM to obtain blood samples for cholesterol analysis using standard procedures. Statistical differences between mean cholesterol 25 values for the same vehicle are determined using analysis of variance followed by Fisher's least significant test.

In therapeutic use as agents for treating hypercholesterolemia or atherosclerosis, the compounds of Formula I are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about five to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methylcellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of this invention are prepared by various means. The compounds of this invention are prepared as generally set forth in Chart I wherein the various symbols Ar, Ar', Z and W have the meanings defined in Formula I. The chiral or racemic amine (1) is protected, e.g., by treatment with t-butoxycarbonyl anhydride in tetrahydrofuran using dimethylaminopyridine as a catalyst after which the protected amine (2) is treated with methane sulfonyl chloride in a suitable solvent such as methylene chloride in the presence of a tertiary amine such as triethylamine, diisopropyl ethyl amine, or pyridine to give the mesylate (3) which is treated with sodium azide in a suitable solvent such as dimethylformamide, with heating to temperatures of from 70° to 95° C. for from 3 to 6 hours. The resulting azide (4) is reduced using for example, lithium aluminum hydride to give the amine (5) which is reacted with an appropriate chloroformate of the formula Ar'OC(=O)Cl to give the protected carbamate (6). The protected carbamate (6) is then deprotected by hydrogen chloride gas in $CH_2Cl_2$ to give the HCl salt of compounds (7) which is converted to compounds (8) by alkylation or acylation.

To obtain compounds (8) wherein Z is

the amine (7) is treated with an acid anhydride of the formula $(RCO)_2O$ wherein R has the meaning defined in Formula I. Additionally, an appropriate acid, $RCO_2H$ or acid halide RCOhalo wherein halo is, e.g., chlorine, may also be used. The reaction is carried out at room temperature in THF and triethylamine. In preparing compounds wherein R is heteroaryl an appropriate heteroarylcarboxylic acid is used with a coupling agent such as carbonyldiimidazole in THF or dicyclohexylcarbodiimide in methylene chloride. The thus obtained amides are final products of the present invention.

To obtain compounds of Formula I wherein Z is $RCH_2$ a compound of formula (7) may be alkylated using an appropriate iodo compound of the formula $RCH_2I$ wherein R has the meaning defined in Formula I or can be reacted with an appropriate aldehyde of the formula RCHO to form an imine which is reduced to the amine (8) using a metal hydride such as sodium borohydride.

To obtain compounds (8) wherein Z represents Ar"

wherein Ar" and X have the meanings defined in Formula I the amine (7) is treated with an appropriate aryl isocyanate or isothiocyanate of the formula Ar"NCX in an aprotic solvent such as methylene chloride or tetrahydrofuran in the presence of a tertiary amine, such as, triethylamine and under an atmosphere of nitrogen.

Alkylation of the amine (7) to obtain compounds (8) wherein W is other than hydrogen is carried out by reacting compounds (7) with an aldehyde of the formula WCHO wherein W has the meaning defined in Formula I to form an imine which is reduced to the amine (8) using a metal hydride such as sodium borohydride in situ. To obtain compounds wherein W is phenyl or substituted phenyl an appropriate arylaldehyde of the formula ArCHO wherein Ar has the meaning defined in Formula I is reacted with aniline or a substituted aniline in the presence of potassium cyanide in acetic acid and methanol under the conditions of a Strecker reaction to give a nitrile of the of formula

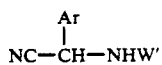

wherein Ar has the meaning defined in Formula I and W' is phenyl or substitued phenyl. The nitrile is hydrolyzed to the corresponding carboxylic acid which is further reduced to the corresponding alcohol which can be substituted for compounds (1) in Chart I.

In preparing compounds (8) wherein W is other than phenyl or subsituted phenyl, it will be readily apparent to one skilled in the art that the substituent groups Z and W can be added in any order.

In preparing compounds of Formula I wherein R represents an alkyl group having from one to six carbon atoms wherein the terminal carbon is substituted with halogen, methoxy, $NR_5R_6$ the appropriate amine is acylated using ω-bromoacyl chloride to give a compound wherein R is —$(CH_2)_m$Br wherein m is an integer of from one to six. The ω-bromoalkyl containing compound can be subjected to various nucleophilic substitutions to give the corresponding compounds wherein the terminal carbon is substituted with methoxy, $NR_5R_6$ or other halogen atoms. The methoxy containing compound is obtained by treating the bromo compound with methanol and sodium hydroxide. The $NR_5R_6$ containing compounds are obtained, e.g., by treating the bromo compound with ammonia gas to give the corresponding ω-$NH_2$ compound, or with dimelhyl amine gas to give the ω-$N(CH_3)_2$ compound or with an excess of an appropriate amine in a lower alcohol solvent at elevated temperature, e.g., 80° to 95° C. to give the corresponding ω—$NR_5R_6$ containing compounds.

The compounds of Formula I as racemates may also be prepared as set forth in Chart II. The aldehyde (1) is reacted with KCN in acetic acid and methanol to give the cyanohydrin (2) which is converted to compounds (3) by alkylation or acylation as generally described hereinabove in Chart I for converting compounds (7) to (8). Additionally compounds of formula (3) wherein Z represents

may be reduced to give compounds of Formula I where $RCH_2$—using a metal hydride such as sodium bis (2-methoxyethoxy) aluminum hydride (Red-Al) in a solvent such as toluene at reflux. The compounds of formula (3) are reduced to compounds (4) using Raney nickel at 50 psi in methanolic ammonia. Compounds (4) are treated with an appropriate chloroformate as generally described hereinabove to give compounds (5). The various symbols Ar, Z, W, and Ar' have the meanings defined in Formula I.

EXAMPLE 1

(R)-(-)-[2-[(1-Oxododecyl)amino]-2-phenylethyl-carbamic acid, 2,6-bis(1-methylethy)phenyl ester (a) R-(-)-α-Phenylglycinol (100 g; 0.729 mole) was dissolved in 2.1 L tetrahydrofuran followed by the addition of tert-butoxycarbonyl anhydride (179.6 g; 0.82 mole) in one portion. 4-Dimethylaminopyridine (91.1 g; 0.74 mole) was then added in portions (foaming). The reaction proceeded overnight after which the solution was concentrated to dryness leaving a cream colored residue. The residue was dissolved in 2.5 L of ethyl acetate and washed with 2×400 mL HCl (1N), 1×400 mL NaOH (1N) and 1×400 mL saturated aqueous sodium chloride. The solution was dried over dryness to give R-(-)-[(1-hydroxymethyl)-1-(phenyl)-methyl]carbamic acid, 2,2-dimethylethyl ester. (b) The product from (a) (121 g; 0.51 mole) was dissolved in 4.0 L of dichloromethane followed by the addition of triethylamine (103 g; 1.02 mole). After cooling to 0° C methane sulfonyl chloride (62.5 g; 0.56 mole) was added dropwise at a rate such that the reaction temperature did not exceed 2° C. The solution was stirred at 0° C. for 1.5 hours then washed with 1 L saturated aqueous sodium chloride. The layers were separated and the organic portion was dried over magnesium sulfate, filtered, and concentrated to dryness. The residue was triturated with hexane and filtered to give (R)-(-)-2-[(methylsulfanyl)oxy]-1-phenylethyl]carbamic acid, 1,1-dimethylethyl ester. (c) The product from (b) (162 g; 0.51 mole) was dissolved in 1620 mL dimethylformamide followed by the addition of sodium azide (165.8 g; 2.55 mole). The mixture was heated to 80° C and stirred for 4 hours. The mixture was then cooled to room temperature followed by the addition of 2 L of water. The product was extracted with 2 X 1.5 L of diethyl ether. The organic solution was dried over magnesium sulfate, filtered, and concentrated to dryness. The liquid was dissolved in 25% ethylacetate/75% hexane and chromatographed on silica gel using 25% ethylacetate/75% hexane as the eluant. The fractions containing the product (first u.v. active spot) were combined and concentrated to dryness yeilding 1,1-dimethylethyl(2-azido-1-phenylethyl)-carbamate as a white solid. (d) To 1.575 L of tetrahydrofuran was added lithium aluminum hydride (21.0 g, 0.55 mole) portionwise under a nitrogen atomsphere. The mixture was cooled to −40° C. followed by the addition of 103 g (0.39 mole) of the product from (c) dissolved in 1 L of tetrahydrofuran. The reaction gradually warmed to 10° C. The mixture was cooled to −35° C. and cautiously quenched with aqueous NaHSO<(71 g/225 ml $H_2O$). The mixture was diluted with 2.0 L ethyl acetate and passed through a pad of celite. The filtrate was dried over magnesium sulfate filtered and concentrated to dryness to give R-(-)-1,1-dimethylethyl-(2-amino-1-phenylethyl)carbamate. (e) The product from (d) (2.5 g;

10.5 m mole) was dissolved in 35 mL of tetrahydrofuran containing triethylamine (1.74 g; 17.2 m mole) followed by the addition of 2,6-diisopropylphenylchloroformate (4.16 g; 10.7 m mole) in one portion. The reaction proceeded for 1 hour, and the precipitate was removed by filtration and washed thoroughly with tetrahydrofuran. The filtrate was concentrated to dryness leaving a white solid. The product was triturated with hexane and collected by filtration to give (R)-(-)-N-[2-[[2,6-bis(1-methylethyl)phenoxy]-carbonyl]amino]-1-phenylethyl-carbamic acid, 1,1-dimethylethyl ester. M.P. 199–200° C. (f) The product from (e) (3.1 g; 7 m mole) was slurried in dichloromethane followed by dissolution upon the addition of HCl gas. Addition of HCl gas was stopped 30 minutes into the reaction, and the precipitate was collected by filtration and washed with hexane to give 2,6-bis(1-methylethyl)phenyl (2-amino-2-phenylethyl)-carbamate HCl salt. (g) The product from (f) (1.0 g; 2.9 m mole) was slurried in 25 mL tetrahydrofuran followed by the addition of triethylamine (0.6 g; 6.1 m mole) in one portion under a nitrogen atmosphere. The mixture was stirred for 30 minutes, filtered, and to the filtrate was added lauroyl chloride (0.69 g; 3.2 m mole) in one portion. The reaction proceeded for 1 hour. The precipitate was removed by filtration and the filtrate was diluted with an equal volume of diethyl ether. The solution was washed with HCl (1N), NaOH(1N), and saturated aqueous NaCl, dried over magnesium sulfate, filtered, and concentrated to dryness to give (R)-(-)-2-[(1-oxododecyl)amino]-2-phenylethyl]-carbamic acid, 2,6-bis(1-methylethyl)phenyl ester as a white solid. M.P. 144–146° C.

EXAMPLE 2

(±)-[2-[(1-Oxodecyl)amino]-2-phenylethyl]carbamic acid, 2,6-bis(1-methylethyl)phenyl ester (a) A mixture of phenyl glycinonitrile, hydrochloride (9.0 g; 23.7 m mole) and triethylamine (5.0 g; 49 m mole), in 80 mL of tetrahydrofuran was stirred for 5 minutes then filtered. To the filtrate was added decanoyl chloride (4.77 g; 25 m mole) in one portion. The mixture was stirred for 30 minutes and filtered. The filtrate was diluted with ethyl acetate, washed with HCl (1N), NaOH(1), saturated aqueous NaCl, dried over magnesium sulfate, filtered, and concentrated to dryness to give (±)-N-(cyanophenyl-methyl) decanamide. (b) The product from (a) (6.1 g; 21.3 m mole) was combined with Raney nickel (5 g) and 150 mL methanolic ammonia at 50 psi after which the mixture was concentrated in vacuo leaving a green oil. The oil crystallized on standing over the weekend from ethylacetate/hexane to give (±)-N-(2-amino-1-phenylethyl)-decanamide. (c) The product from (b) (0.74 g; 2.5 m mole) was dissolved in 10 mL tetrahydrofuran followed by the addtion of triethylamine (0.25 g; 2.5 m mole). 2,6-Diisopropylphenylchloroformate (1.0 g; 2.5 m mole) was added in one portion. The reaction proceeded for 1 hour, and the insoluble material was removed by filtration and washed with tetrahydrofuran. The filtrate was concentrated to dryness, and the residue was triturated with hexane and filtered to give (±)2-[(1-oxodecyl)amino]-2-phenylethyl]carbamic acid, 2,6-bis(1-methylethyl)phenyl ester. M.P. 189–190° C.

EXAMPLE 3

2,6-Diisopropylphenylchloroformate 2,6-Diisopropylphenol (8.9 g; 0.05 mole) was dissolved in 35 mL benzene and cooled to −3° C. after which liquid phosgene (7.0 mL condensed at −70° C.) was added dropwise maintaining a temperature range of 0° to 3° C. N,N-dimethylaniline (6.0 g; 12.2 m mole) was added dropwise and stirred at 0° C. for 15 minutes. The yellow green suspension was quenched with 5 mL water and the layers were separated. The organic portion was washed with HCl (1N, 5 mL), saturated aqueous NaCl, dried over magnesium sulfate, filtered, and concentrated to dryness to give a green liquid which was distilled affording 2,6-diisopropylphenyl chloroformate as a yellow liquid.

CHART I

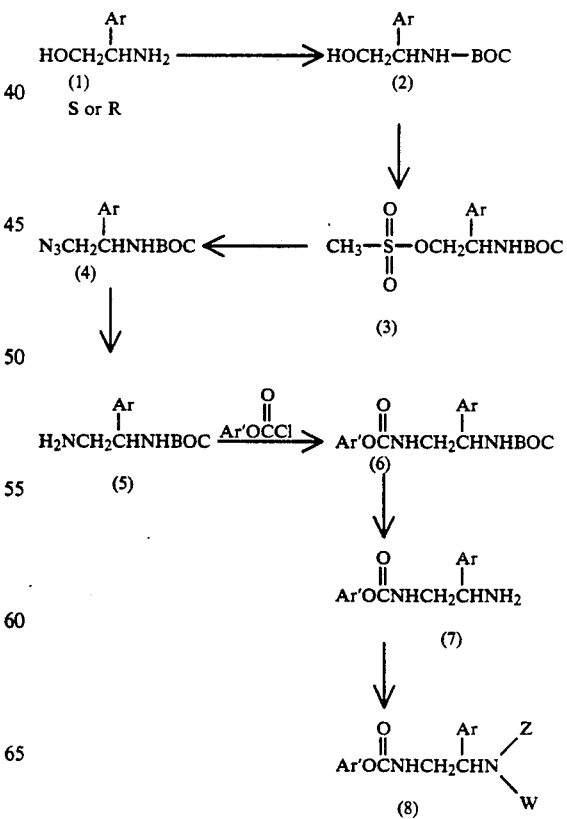

CHART II

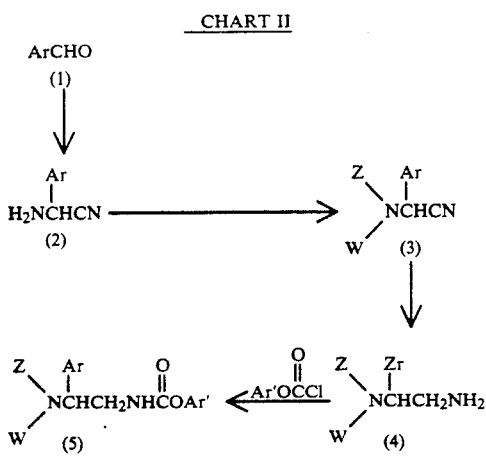

We claim:
1. A compound of the formula

wherein of Ar is selected from:
  phenyl which is unsubstituted or is substituted with from one to three substituents selected from
  alkyl having from one to six carbon atoms and which is straight or branched,
  alkoxy having from one to six carbon atoms and which is straight or branched,
  phenoxy,
  hydroxy,
  fluorine,
  chlorine,
  bromine,
  nitro,
  trifluoromethyl,
  —COOH
  —COOalkyl wherein alkyl has from one to four carbon atoms
  —$NR_1R_2$ wherein $R_1$ and $R_2$ are independently hydrogen or alkyl of from one to four carbon atoms;
wherein Ar' is selected from:
  phenyl which is unsubstituted or is substituted with from one to three substituents selected from alkyl having from one to six carbon atoms and which is straight or branched; alkoxy having from one to six carbon atoms and which is straight or branched,
  phenoxy,
  hydroxy,
  fluorine,
  chlorine,
  bromine,
  nitro,
  trifluoromethyl,
  —COOH,
  —COOalkyl wherein alkyl has from one to four carbon atoms
  —$NR_1R_2$ wherein $R_1$ and $R_2$ are independently hydrogen or alkyl of from one to four
wherein Z is

wherein R is selected from:
  (a) a straight or branched hydrocarbon chain having from one to twenty carbon atoms and which is saturated or contains from one to three double bonds;
  (b) a straight or branched hydrocarbon chain having from one to six carbon atoms wherein there terminal carbon atom is substituted with chlorine, fluorine, bromine, straight or branched lower alkoxy having from one to four carbon atoms, straight or branched thioalkoxy having from one to four carbon atoms, a $COOR_4$ group wherein $R_4$ is hydrogen or a straight or branched alkyl having from one to four carbon atoms, an —$NR_5R_6$ group wherein $R_5$ and $R_6$ are independently hydrogen or lower alkyl having from one to four carbon atoms, wherein said alkyl is unsubstituted or substituted with hydroxy, or wherein —$NR_5R_6$ taken together form a monocyclic heterocyclic group selected from pyrrolidines, piperidine, piperzaine or piperazine substituted in the 4-position with a lower alkyl having from one to four carbon atoms or —$COOR_4$ wherein $R_4$ has the meaning defined above; and
  (c) a 5- or 6- membered monocyclic or fused bicyclic teterocycle containing at least one to four nitrogen, oxygen or sulfur atoms in at least one ring member;
  (d) the group

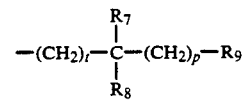

wherein t is zero to four; p is zero to four with the proviso that the sum of t and p is not greater than five; $R_7$ and $R_8$ are independently selected from hydrogen or alkyl having from one to six carbon atoms, or when $R_7$ is hydrogen, $R_8$ can be the same as $R_9$ and $R_9$ is phenyl or phenyl substituted with from one to three substituents selected from straight or branched alkyl having from one to six carbon atoms, straight or branched alkoxy having from one to four carbon atoms, straight or branched thioalkoxy having from one to four carbon atoms, phenoxy, hydroxy, fluorine, chlorine, bromine, nitro, trifluoromethyl, —COOH, COO alkyl wherein alkyl has from one to four carbon atoms, or —$NR_5R_6$ wherein $R_5$ and $R_6$ have the meanings defined above; and
  (e) phenyl or phenyl substituted with from one to three substitutes selected form straight or branched alkyl having from one to six carbon atoms, straight or branched alkoxy having from one to four carbon atoms, straight or branched thioalkoxy having from one to four carbon atoms, phenoxy, hydroxy, fluorine, chlorine, bromine, nitro, trifluoromethyl, —COOH, COOalkyl wherein alkyl has from one to four carbon atoms, or —$NR_5R_6$ wherein $R_5$ and $R_6$ have the meanings defined above; or a pharmaceutically acceptable salt or an N-oxide thereof.

2. A compound of claim 1 wherein Ar' is phenyl.
3. A compound of claim 2 wherein Ar' is phenyl disubstituted in the 2,6- positions.
4. A compound of claim 1 which is
   (R)-[2[(1-oxododecyl)amino[-2-phenylethyl]-carbamic acid, 2,6-bis(1-methylethyl)phenyl ester; or
   (±)-[2-[(1-oxododecyl)amino[-2-phenylethyl]-carbamic acid, 2,6-bis(1-methylethyl)phenyl ester.

* * * * *